(12) United States Patent
Harbeck

(10) Patent No.: US 6,589,537 B2
(45) Date of Patent: Jul. 8, 2003

(54) INFANT SKIN CARE COMPOSITION

(76) Inventor: Marie Harbeck, 3202 Clumpgrass Cove, Austin, TX (US) 78735

( * ) Notice: Subject to any disclaimer, the term of this patent is extended or adjusted under 35 U.S.C. 154(b) by 0 days.

(21) Appl. No.: 09/753,895

(22) Filed: Jan. 3, 2001

(65) Prior Publication Data

US 2001/0006666 A1 Jul. 5, 2001

Related U.S. Application Data

(63) Continuation-in-part of application No. 09/248,573, filed on Feb. 11, 1999, now Pat. No. 6,193,987.

(51) Int. Cl.$^7$ .......................... A61K 9/00; A61K 35/78; A61K 31/355; A01N 65/00; A01N 31/04
(52) U.S. Cl. ..................... 424/400; 424/727; 424/735; 424/736; 424/747; 424/768; 514/458; 514/725
(58) Field of Search ............................. 424/400, 727, 424/735, 736, 747, 768; 514/458, 725

(56) References Cited

U.S. PATENT DOCUMENTS

| 4,556,560 A | | 12/1985 | Buckingham | ............... | 424/641 |
|---|---|---|---|---|---|
| 4,608,392 A | * | 8/1986 | Jacquet et al. | | |
| 4,740,367 A | * | 4/1988 | Force et al. | ................... | 424/47 |
| 4,816,254 A | | 3/1989 | Moss | ......................... | 424/642 |
| 4,857,321 A | | 8/1989 | Thomas | ....................... | 424/525 |
| 4,883,659 A | * | 11/1989 | Goodman et al. | | |
| 5,244,679 A | * | 9/1993 | Freston | ....................... | 424/659 |
| 5,431,911 A | * | 7/1995 | Reynolds | | |
| 5,489,429 A | * | 2/1996 | Griet et al. | .................. | 424/401 |
| 5,618,529 A | | 4/1997 | Pichierri | .................. | 424/78.06 |
| 5,683,704 A | * | 11/1997 | Ohba et al. | ................. | 424/401 |

* cited by examiner

*Primary Examiner*—Sreeni Padmanabhan
*Assistant Examiner*—Michael A Willis

(57) ABSTRACT

A resistant to body fluids, organic oil-based topical transdermal composition for the alleviation and treatment of infant skin conditions, including, dry, sensitive, chapped, cracked, itching reddened, and flaking skin, as well as infant skin infirmities associated with eczema, dermatitis, and diaper rash, which has as main constituents, organic oil lipids, vitamin A, tocopheral linoleate, and tincture of benzoin, in an organic beeswax emulsifying base.

4 Claims, No Drawings

INFANT SKIN CARE COMPOSITION

This invention is a "Continuation-In-Part" Application for Ser. No. 09/248,573 filed Feb. 11, 1999, for Marie Harbeck, now U.S. Pat. No. 6,193,987 B1.

BACKGROUND OF INVENTION

This invention relates to an improved and useful organic oil-based topical transdermal composition for the alleviation and treatment of infant skin conditions, including, dry, sensitive, chapped, cracked, itching, reddened, and flaking skin, as well as infant skin infirmities associated with eczema, dermatitis, and diaper rash, which has as its main constituents, safflower oil, flaxseed oil, vitamin A, tocopheral linoleate, sweet almond oil, apricot kernel oil, essential oil of lavender, and tincture of benzoin, in an organic beeswax emulsifying base.

To the best of the applicant's knowledge the following is the most relevant prior art:

| U.S. Pat. No. 4,740,367 | Force, et al. | 1988 |
| U.S. Pat. No. 5,244,679 | Freston. | 1993 |
| U.S. Pat. No. 5,489,429 | Griat, et al. | 1996 |
| U.S. Pat. No. 5,683,704 | Ohba, et al. | 1997 |
| U.S. Pat. No. 4,883,659 | Goodman, et al. | 1989 |
| U.S. Pat. No. 4,608,392 | Jacquet et al. | 1986 |
| U.S. Pat. No. 5,431,911 ] | Reynolds. | 1995 |
| U.S. Pat. No. 4,857,321 | Thomas. | 1989 |
| U.S. Pat. No. 4,816,254 | Moss. | 1989 |
| U.S. Pat. No. 4,816,254 | Moss. | 1989 |
| U.S. Pat. No. 4,556,560 | Buckingham. | 1985 |
| U.S. Pat. No. 5,618,529 | Pichierri. | 1997 |
| Foreign Patent Documents | | |
| 40048556 EP. | | 1982 |
| 0260859 EP. | | 1988 |
| 2080682 GB. | | 1981 |

The pharmaceutical industry is continually expanding its efforts in order to provide infant topical preparations which will eliminate and prevent diaper rash, cracking, chapping, chaffing, redness and restore the skin to its natural healthy condition, thus the combinations of skin aggravating synthetic compositions employed continue to increase yearly.

Thus, synthetic surfactants, silicones, ammonia, alcohol's, solvents, acids, artificial colors, animal oils, mineral oils, petrolatum derivatives, fungicides, plant resins, oxides, plus cadmium, cobalt, lead, mercury, molybdenum, nickel, silver, tin, zinc and iron salts, nitrates, chlorides, and fragrances, and the like are being incorporated into the compositions of the cited prior art compositions that are supplied to stores and supermarkets.

It will be appreciated that the expansion and growth of the cited prior art has devolved into highly complex synthetic adjuvants for use in the formulations.

The problem with the use of the compositions of the cited prior art which make up the bulk of transdermal delivery systems are their chemical structures which are known to cause skin irritations.

Synthetic surfactants, silicones, ammonia, alcohol's, solvents, acids, artificial colors, animal oils, mineral oils, petrolatum derivatives, fungicides, plant resins, oxides, plus cadmium, cobalt, lead, mercury, molybdenum, nickel, silver, tin, zinc and iron salts, nitrates, chlorides, and fragrances, incorporated into the compositions of the prior art cause rashes, allergies, and dermatitis of the skin.

Unfortunately, the cited prior art compositions are relatively ineffective for treatment of infant dermatitic skin conditions, including the treatment and alleviation of skin irritations related to allergic skin reactions to synthetic adjuvants, so there is a need for organic compounds for improved skin care compositions.

The said prior art compositions do not employ massive quantities of cold-pressed organic vegetable oils.

The said prior art compositions do not employ organic beeswax compositions that this invention incorporates.

In terms of effectiveness, the said cited prior art compositions do not provide satisfactory skin penetration and supplying properties to leave skin satiny smooth for up to twelve hours.

The said cited prior art compositions do not provide the high volume of cold pressed organic safflower oil, or flaxseed oil, in their formulas to restore essential oil lipids that are essential to nourish and maintain healthy skin.

The said cited prior art compositions do not provide the high volume of skin healing vitamin A and tocopheral linoleate compositions to their formulations.

The said cited prior art compositions do not include tincture of benzoin in their formulations.

The said cited prior art compositions do not boil tincture of benzoin to eliminate its alcohol content.

The said cited prior art compositions do not provide an urgent need that exists for compositions like the present invention for use in the dermatological, pharmaceutical, and alternative therapy fields.

The said cited prior art compositions do not provide organic compositions to alleviate and treat the symptoms of infant dermatitic skin infirmities.

The said cited prior art compositions do not provide organic moisturizing compositions that provide a water resistant, non-greasy, antiseptic film on the skin.

The said cited prior art compositions do not provide organic compositions that are water resistant to body fluids.

The said cited prior art compositions do not provide organic compositions to provide organic essential oil for its anti-inflammatory qualities and to perfume the said compositions.

The said cited prior art compositions do not provide a high volume of organic safflower and flaxseed oils in the said compositions.

The said cited prior art compositions do not provide high volume organic compositions to replace lost oil lipids to the dermis.

The said cited prior art compositions do not provide gentle, organic compositions for infant use.

Objectives and advantages of the present invention are:

a) to provide an alcohol free topical skin preparation, b) to provide an essential plant oil as an organic antiseptic adjuvant to treat bacterial, and fungal conditions of the skin;

c) to provide a topical skin composition that has potent effectiveness in the treatment of infant skin infirmities, such as dermatitis, eczema, chapping, cracking, flaking, redness, and skin allergies related to synthetic substances and the like;

d) to provide a high volume of organic cold pressed vegetable oil compositions for immediate transdermal delivery, e) to provide a satisfactory skin penetration of the said composition and supplying properties that protect the skin for up to twelve hours, f) to provide organic essential oil to perfume the said composition, g) to provide a high volume of organic safflower and flaxseed oils in the said composition to replace oil lipids to the dermis, h) to provide an urgent need that exists for composition like the present invention for the dermatological, pharmaceutical, and alternative therapy fields, i) to alleviate and treat the symptoms of dermatitis, cracking, eczema, chapping, and allergic skin reactions due to ammonia, solvents, acids, alcohol substances, animal oils, mineral oils, petrolatum derivatives, fungicides, plant resins, oxides, plus cadmium, cobalt, lead, mercury, molybdenum, nickel, silver, tin, zinc and iron salts, nitrates, chlorides, and artificial fragrances, that are incorporated into the compositions of the cited prior art;

j) to provide an organic beeswax substance that bonds lubricating, hydrating, moisturizing and antiseptic compounds to the skin for up to twelve hours, k) to provide an organic skin calming composition to infants skin, l) to provide a gentle, organic composition to treat and alleviate the symptoms of infant diaper rash, m) to provide an organic non-greasy, antiseptic and moisturizing film on the skin, n) to provide an organic composition that is water resistant to body fluids, o) to provide an organic composition without chemical structures that are known to cause skin irritations, p) to provide an organic composition without solvents, artificial perfumes, artificial colorants and ammonia additives;

q) to provide an organic treatment composition without ammonia, solvents, acids, substances, mineral oil, petrolatum derivatives, plant resins, oxides, plus cadmium, cobalt, lead, mercury, molybdenum, nickel, silver, tin, zinc and iron salts, nitrates, chlorides, and artificial fragrances, that are incorporated into the compositions of the cited prior art Thus, an urgent need exists for a skin composition like the present invention, that employs a high volume of potent cold-pressed organic flaxseed and safflower oils plus organic vitamins to feed the skin with nutritive polyunsaturated oil lipids without the addition of skin irritating synthetic adjuvants. Further advantages of this invention are the employment of an organic wax substance and an organic antiseptic substance that bonds to the skin, leaving the skin moisturized and in a healthy condition for up to twelve hours. Still further objects and advantages will become apparent from a consideration of the ensuing descriptions.

BRIEF SUMMARY OF THE INVENTION

An improved, and useful, water resistant to body fluids, organic oil-based topical transdermal composition for the swift alleviation and treatment of infant skin conditions, including, dry, sensitive, chapped, cracked, itching, reddened, and flaking skin, as well as infant skin infirmities associated with eczema, dermatitis, allergic skin reactions to synthetic adjuvants, and diaper rash, which has as main constituents, safflower oil, flaxseed oil, vitamin A, tocopheral linoleate, sweet almond oil, apricot kernel oil, essential oil of lavender, and tincture of benzoin, in an organic beeswax emulsifying base.

DESCRIPTION OF THE INVENTION

It is an objective of the improved invention to provide a potent, swift acting, non-sticky, organic, transdermal delivery formulation for treating and alleviating dry, distressed skin conditions, including dermatitis, eczema, rough skin, cracking, itching, peeling, redness, and allergic skin reactions.

It is an objective of the improved invention to provide an improved formulation which soothes, moisturizers and restores essential nutrients to the skin to improve its texture and protect it against dryness.

It is an objective of the improved invention to provide an alcohol free topical skin preparation.

It is an objective of the improved invention to provide an essential plant oil as an organic antiseptic adjuvant to treat bacterial, and fungal conditions of the skin.

It is an objective of the improved invention to provide a topical skin composition that has potent effectiveness in the treatment of infant skin infirmities, such as dermatitis, eczema, chapping, cracking, flaking, redness, and skin allergies related to synthetic substances and the like.

It is an objective of the improved invention to provide a high volume of organic cold pressed vegetable oil compositions for immediate transdermal delivery.

It is an objective of the improved invention to provide a satisfactory skin penetration of the said composition and supplying properties that protect the skin for up to twelve hours.

It is an objective of the improved invention to provide organic essential oil to perfume the said composition.

It is an objective of the improved invention to provide a high volume of organic safflower and flaxseed oils in the said composition to replace oil lipids to the dermis.

It is an objective of the improved invention to provide an urgent need that exists for composition like the present invention for the dermatological, pharmaceutical, and alternative therapy fields.

It is an objective of the improved invention to alleviate and treat the symptoms of dermatitis, cracking, eczema, chapping, and allergic skin reactions due to ammonia, solvents, acids, alcohol substances, mineral oils, petrolatum derivatives, fungicides, plant resins, oxides, plus cadmium, cobalt, lead, mercury, molybdenum, nickel, silver, tin, zinc and iron salts, nitrates, chlorides, and artificial fragrances.

It is an objective of the improved invention to provide an organic beeswax substance that bonds lubricating, hydrating, moisturizing and antiseptic compounds to the skin for up to twelve hours.

It is an objective of the improved invention to provide an organic skin calming composition to infants skin.

It is an objective of the improved invention to provide a gentle, organic composition to treat and alleviate the symptoms of infant diaper rash.

It is an objective of the improved invention to provide an organic non-greasy, antiseptic and moisturizing film on the skin.

It is an objective of the improved invention to provide an organic composition that is water resistant to body fluids.

It is still a further objective of the improved invention to provide an organic composition without chemical structures that are known to cause skin irritations.

These and other other objectives are accomplished in accordance with a particular embodiment of the present improved invention which provides a skin care composition in the form of a cream, comprising a mixture consisting of tincture of benzoin lanolin, cetearyl alcholol & polysorbate 60, vitamins A, tocopheral linoleate, organic beeswax, cold-pressed flaxseed, wheatgerm, and safflower oils, glycerin, borax, stearic acid, and essential oil of lavender or similar perfuming compounds and mixtures thereof.

The present improved invention includes the surprising discovery that cold-pressed organic safflower and flaxseed oils, tincture of benzoin, vitamin A and tocopheral linoleate, can be used as active principals in the improved skin care composition to treat infant skin conditions attributed to eczema, dermatitis, chapped, cracked, reddened, and distressed skin conditions, including diaper rash. In accordance with the present improved invention there is provided a formulation where cold-pressed, organic safflower oil, flaxseed oil, and tincture of benzoin can be employed with organic beeswax to aid in the water-resistant, non-greasy, treatment and alleviation of infant skin conditions. Embodiments of the improved invention follow to illustrate the formulation.

The main embodiment of this cream are:

20 to 300 milliliters water, 10 to 80 grams cetearyl alcohol & polysorbate 60 called LipowaxP, purchased from Lipo Chemicals Inc,207 19th Avenue, Paterson, N.J. 07504;

5 to 80 grams organic white beeswax, 5 to 160 milliliters cold-pressed safflower oil, 5 to 160 milliliters sweet almond oil, 5 to 160 milliliters cold-pressed flaxseed oil, 2 to 130 milliliters apricot kernel oil, 1 to 130 milliliters jojoba oil, 1 to 85 grams cocoa butter, 2.5 milliliters tocopheral linoleate, 2.5 grams borax granules, 0.5 to 20 milliliters of a perfuming compound chosen from a group comprising: essential oil of lavender, peppermint, rosemary, chamomile, peach, neroli, ginger, almond, spearmint, violet, sandalwood, musk, magnolia, citrus, orange, lemon, vanilla, papaya, verbena, rose, thyme, borage, sage, pine and cedar;

0.1 to 20 milliliters composition containing 15000 micrograms of vitamin A/ml, 0.1 to 20 milliliters tincture of benzoin, 0.1 to 5 milliliters dmdm hydantoin, My lotion mixing process is as follows:

place safflower oil, sweet almond oil, apricot kernel oil, tocopheral linoleate, vitamin A, jojoba oil, flaxseed oil, cetearyl alcohol and polysorbate 60, beeswax, and cocoa butter in a partially submerged container over hot water to form a mixture, stirring said mixture over hot water until dissolved, simultaneously placing water, borax and tincture of benzoin, in another partially submerged container over hot water to form a mixture:

stirring said mixture over hot water until dissolved, removing said mixtures from heat and blending by stirring both mixtures until the new said mixture cools to approximately 40 degrees C;

adding essential oil of lavender or other perfuming compound and dmdm hydantoin to said new mixture, and blending the final mixture with stirring until it thickens, whereby the ingredients are formed into a cream.

While we believe that the antiseptic, protective, softening, water resistant, long term lubricating properties and the high volume of organic cold-pressed flaxseed oil lipids, and organic cold-pressed safflower oil lipids, and the volume of vitamin A, tocopheral linoleate, and tincture of benzoin, emulsified in organic beeswax are responsible for the alleviation, and treatment of infant dermatitis, eczema, chapped, dry, cracked, and reddened skin infirmities, including diaper rash, we don't wish to be bound by this.

As noted, the improved composition hereof comprises a water-resistant, topical application which is applied to the dermal areas of the body to alleviate and treat dermatitis, eczema, dry, chapped, flaky, rough, reddened, cracked, and diaper rash skin conditions, by feeding skin the essential polyunsaturated oil lipids the skin needs to maintain its healthy condition.

This improved formulation is highly effective for pharmaceutical use in the treatment and alleviation of dermatitis, eczema and dry skin due to the resistance of the formulation to attack by body fluids, perspiration, and body acids.

This improved formulation treats and alleviates skin irritations without the use of ammonia, solvents, acids, alcohol substances, mineral oils, petrolatum derivatives, plant resins or gums, oxides, plus cadmium, cobalt, lead, mercury, molybdenum, nickel, silver, tin, zinc and iron salts, nitrates, chlorides, and artificial fragrances.

This improved formulation provides a water-resistant, light-weight cream that is preferred to be used as an infant skin protectant.

This improved formulation employs organic polyunsaturated oil lipids in the place of mineral oil, which by its solvent action strips skin surface lipids.

This improved formulation employs organic cocoa butter as a dermal lubricant and fluid resistant skin barrier in the place of petrolatum used in many compositions, which by its solvent property leaves a sticky residue on the skin.

This improved formulation leaves a silky, invisible barrier upon the skin, by its swift skin penetrating properties.

This improved formulation treats infant skin irritations more efficiently and effectively without chemical structures that are known to cause skin irritations.

This improved formulation provides an organic skin composition that enables the healing process to occur and prevents any additional skin irritation.

This improved formulation penetrates the dermis immediately and leaves no residue, so it does not stain clothing.

This improved formulation has a low melting point, thereby eliminating and preventing skin drag on sensitive and irritated skin.

For a more complete understanding of the present improved composition reference is made to the following examples. The following examples are illustrative of the present improved composition and are not intended in any manner as a limitation upon the scope thereof.

EXAMPLE 1

The composition of the cream was applied after each diaper change to the buttocks of a 12 month old infant suffering from chaffed and reddened skin. Within two days use, the chaffing and redness began to resolve. After 3 days, no sign of chaffing or redness were visible.

EXAMPLE 2

Compared to commercially available infant skin formulation, the results based upon the efficacy of the present invention are set forth hereinafter: A female child was bothered by frequent diarrhea, which resulted in scalding of her skin around the diaper area. Several therapies had been tried without success. After three applications of the improved present invention, an improvement in the skin was visible. After 24 hours, no sign of redness was visible.

EXAMPLE 3

The composition of the present invention was applied twice daily to the skin of a three month old baby suffering from eczema. Within two days, the dry, flaky skin on her cheeks was replaced by pink new skin. After seven days use, no sign of the rash was visible.

EXAMPLE 4

The present invention was applied to the diaper area of an infant suffering from diaper rash. After each diaper change, the skin was cleansed with warm water and the present invention was reapplied. Within 24 hours, improvement was seen and the diaper rash healed after two days.

From the preceding it will be readily perceived by the reader that an urgent need exists for this improved composition for the prevention, alleviation and treatment of infant skin conditions denoted heretofore.

The improved composition provides:

an alcohol, silicone and solvent free formulation, organic antiseptic adjuvants to fight bacterial skin infirmities, a topical composition that has immediate effectiveness in the treatment of infant dermatitic skin infirmities, superior skin penetration of the said composition and nutrient supplying properties, high volumes of organic polyunsaturated oils to replace lost dermal lipids, a composition to fill an urgent need in the pharmaceutical, and alternative health markets, organic beeswax to bond lubricating, hydrating, antiseptic and moisturizing compounds to the skin, organic calming, moisturizing compounds to skin to alleviate diaper rash, a composition that does not strip the skin of its natural oils, a non-greasy moisturizing film on the skin that is resistant to attack by body fluids, a soft spreading cream that is preferred for sensitive infant skin, and organic oil lipids in the place of mineral oil, which by its solvent action strips skin surface lipids.

While the above description contains many specificity's, these should not be construed as limitations on the scope of the improved invention, but merely providing illustrations of some of the presently preferred embodiments of this improved invention.

Many other variations are possible. For example, it is additionally possible to add to the present invention many other adjuvants such as additional organic perfuming ingredients chosen from a group comprising essential oil of lavender, peppermint, orange, lemon, grapefruit, spearmint, rosemary, violet, sandalwood, musk, magnolia, citrus, vanilla, gardenia, papaya, peach, rose, verbena, lilac, rosewood, neroli, ginger, almond, and the like, vitamins, antibiotics, lanolin, vegetable and plant oils, floral waters, and anti-inflammatory additives, and be within the purview of the invention.

Accordingly, the scope of the invention should be determined by the specifications and by the appended claims and their legal equivalents, rather than just by the examples given.

What is claimed is:

1. A cream comprising:
from 30 to 175 milliliters water,
from 10 to 80 grams cetearyl alcohol & polysorbate 60,
from 5 to 80 grams organic beeswax,
from 5 to 160 milliliters safflower oil,
from 5 to 160 milliliters sweet almond oil,
from 2 to 80 milliliters flaxseed oil,
from 2 to 130 milliliters apricot kernel oil,
from 2 to 110 milliliters jojoba oil,
from 1 to 85 grams cocoa butter,
from 0.2 to 55 milliliters tocopheral linolcate,
from 0.1 to 20 grams borax granules,
from 0.5 to 10 milliliters of a perfuming compound selected from a group consisting of oil of lavender, peppermint, orange, lemon, grapefruit, spearmint, rosemary, violet, sandalwood, musk, magnolia, citrus, vanilla, gardenia, papaya, peach, rose, verbena, lilac, rosewood, neroli, ginger, almond,
from 0.1 to 10 milliliters composition containing 15,000 micrograms vitamin A/ml, from 0.1 to 20 milliliters tincture of benzoin, and from 0.1 to 5 milliliters dmdm hydantoin.

2. A cream as in claim 1 further comprising approximately 0.1 to 20 milliliters of wheatgerm oil.

3. A cream comprising:
90 milliliters water,
60 grams cetearyl alcohol & polysorbate 60,
30 grams organic beeswax,
60 milliliters cold-pressed safflower oil,
60 milliliters sweet almond oil,
30 milliliters cold-pressed flaxseed oil,
30 milliliters apricot kernel oil,
10 milliliters jojoba oil,
15 grams lanolin,
2.5 milliliters tocopheral linoleate,
2.5 grams borax granules,
2.5 milliliters essential oil of lavender,
1.25 milliliters composition containing 15,000 micrograms vitamin A/ml,
0.5 milliliters tincture of benzoin, and
0.6 milliliters dmdm hydantoin.

4. A method of making a cream comprising:
placing safflower oil, sweet almond oil, apricot kernel oil, tocopheral linoleate, jojoba oil, flaxseed oil, cetearyl alcohol & polysorbate 60, beeswax, vitamin A, cocoa butter in a partially submerged container over hot water to form a mixture;
stirring said mixture over hot water until dissolved,
placing water, borax and tincture of benzoin, in another partially submerged container over hot water to form a mixture;
stirring said second mixture over hot water until dissolved, to burn off alcohol content of tincture of benzoin,
removing said mixtures from heat and blending both mixtures until said mixtures cool to 40 degrees C;
adding a perfuming agent, and dmdm hydantoin to said mixture,
and blending said mixture until it thickens,
whereby the ingredients are formed into a cream.

* * * * *